(12) United States Patent
Velardi (10) Patent No.: US 7,544,355 B2
(45) Date of Patent: Jun. 9, 2009

(54) METHODS AND COMPOSITIONS FOR ALLOGENEIC TRANSPLANTATION

(75) Inventor: Andrea Velardi, Perugia (IT)

(73) Assignee: Universita Degli Studi di Perugia, Perugia (IT)

( * ) Notice: Subject to any disclaimer, the term of this patent is extended or adjusted under 35 U.S.C. 154(b) by 69 days.

(21) Appl. No.: 10/384,770

(22) Filed: Mar. 11, 2003

(65) Prior Publication Data

US 2004/0019390 A1 Jan. 29, 2004

Related U.S. Application Data

(60) Provisional application No. 60/363,575, filed on Mar. 13, 2002.

(51) Int. Cl.
*A01N 63/00* (2006.01)
(52) U.S. Cl. .................................. 424/93.1; 424/93.7
(58) Field of Classification Search ................. None
See application file for complete search history.

(56) References Cited

U.S. PATENT DOCUMENTS 6,103,694 A * 8/2000 Mardiney et al. ............ 514/12

OTHER PUBLICATIONS

Ciccone et al, J Exp Med. Mar. 1, 1992;175:709-18.*
Ruggeri et al, Curr Opin Hematol 2001;8:355-9.*
Murphy et al, J Immunol 1992;148:2953-60.*
Ruggeri et al, Transplant Immunol 2005;14:203-6.*
Davies et al, Blood 2002;100:3825-7.*
Malmberg et al., Mol Immunol 2005;42:531-4.*
Asai, et al., Suppression of Graft-Versus-Host Disease and Amplification of Graft-Versus-Tumor Effects by Activated Natural Killer Cells after Allogeneic Bone Marrow Transplantation, The Journal of Clinical Investigation, vol. 101, No. 9, (May 1998), 1835-1842.
Ruggeri, et al., Role of Natural Killer Cell Alloreactivity in HLA-Mismatched Hematopoietic Stem Cell Transplantation, Blood, vol. 94, No. 1 (Jul. 1999), pp. 333-339.
Ruggeri, et al., Effectiveness of Donor Natural Killer Cell Alloreactivity in Mismatched Hematopoietic Transplants, Science, vol. 295, (Mar. 2002), pp. 2097-2100.

Ruggeri et al. Donor natural killer cell allorecognition of missing self in haploidentical hematopoietic transplantation for acute myeloid leukemia: challenging its predicitve value. Blood, 2007; 110: 433-440.
Beelen DW, Hottinger HD, Ferencic S, et al. Genotypic Inhibitory Killer Immunoglobulin-like Receptor Ligand Incompatibility Enhances the Long-term Antileukemic Effect of Unmodified Allogeneic Hematopoietic Stem Cell Transplantation in Patients with Myeloid Leukemias. Blood 2005; 105:2594-2600.
Dawson MA and Spencer A. Successful use of haploidentical stem-cell transplantation with KIR mismatch as initial therapy for poor-risk myelodysplastic syndrome. J Clin Oncol 2005; 23:4473-4474.
Giebel S, Locatelli F, Lamparelli T, et al. Survival advantage with KIR ligand incompatibility in hematopoietic stem cell transplantation from unrelated donors. Blood 2003; 102:814-819.
Elmaagacli AH, Ottinger H, Koldehoff M, et al. Reduced risk for molecular disease in patients with chronic myeloid leukemia after transplantation from a KIR-mismatched donor. Transplantation 2005; 79:1741-1747.
Kroger N, Shaw B, Iacobelli S, et al. Comparison between antithymocyte globulin and alemtuzumab and the possible impact of KIR-ligand mismatch after dose-reduced conditioning and unrelated stem cell transplantation in patients with multiple myeloma. Br J Haematol 2005; 129:631-43.
Cooley S, McCullar V, Wangen R, et al. KIR reconstitution is altered by T cells in the graft and correlates with clinical outcomes after unrelated donor transplantation. Blood 2005; 106:4370-4376.
Igarashi et al, "Enhanced cytotoxicity of allogeneic NK cells with killer immunoglobulin-like receptor ligand incompatibility against melanoma and renal cell carcinoma cells", Blood 2004, vol. 104, No. 1, pp. 170-177.
Ruggeri et al, "Allogeneic hermatopoietic transplantation and natural killer cell recognition of missing self", Immunological Reviews 2006, vol. 214, pp. 202-218.

* cited by examiner

*Primary Examiner*—Q. Janice Li
(74) *Attorney, Agent, or Firm*—Nixon & Vanderhye P.C.

(57) ABSTRACT

The present invention relates, generally, to methods and compositions for allogeneic transplantation. More particularly, the invention relates to the use of alloreactive natural killer cells in order to enhance the efficacy and/or safety of allogeneic grafts in human subjects. The invention allows to increase the engraftment of an allogeneic grafts, even in myelo-reductive conditioning, to protect against GVHD and/or to eradicate malignant cells. The invention is particularly suited in allogeneic hematopoietic transplantations, particularly bone marrow transplantations.

16 Claims, 4 Drawing Sheets

METHODS AND COMPOSITIONS FOR ALLOGENEIC TRANSPLANTATION

The present application claims benefit of U.S. Provisional Application No. 60/363,575, filed Mar. 13, 2002, the entire contents of which is hereby incorporated by reference.

FIELD OF THE INVENTION

The present invention relates, generally, to methods and compositions for allogeneic transplantation. More particularly, the invention relates to the use of alloreactive natural killer cells in order to enhance the efficacy and/or safety of allogeneic grafts in human subjects. The invention allows to increase the engraftment of an allogeneic grafts, even in myelo-reductive conditioning, to protect against GVHD and/or to eradicate malignant cells. The invention is particularly suited in allogeneic hematopoietic transplantations, particularly bone marrow transplantations.

BACKGROUND OF THE INVENTION

Human leukocyte antigen (HLA)-matched allogeneic hematopoietic transplantation has revolutionized the treatment of leukemia, lymphoma, and inherited hematopoietic stem cell diseases (Stockerl-Golstein et al., 1999). Donor T cells contained in the allograft are vital for promoting engraftment, eradicating malignant cells [the graft-versus-leukemia (GVL) effect], and reconstituting immunity. Unfortunately, these cells are known to mediate Graft-versus-host disease ("GVHD"), which is an attack on recipient tissues. GVHD and the global immunosuppression needed to prevent or treat it underlie the major reasons for transplant failures: infection and neoplastic relapse. Furthermore, only 60% of patients have matched sibling or unrelated donors, and even fewer make it to transplant because of the delays due to the donor search and bone marrow harvesting (Martelli et al., 2002). However, virtually every patient has a family member who is identical for one HLA haplotype and fully mismatched for the other, and thus could immediately serve as a donor.

Transplantation across the histocompatibility barrier has been made possible by extensive T cell depletion of the graft to help prevent GVHD, and transplantation of large numbers of hematopoietic stem cells to help overcome rejection (Martelli et al., 2002; Aversa et al., 1994, 1998; Bachar-Lustig et al., 1995; Reisner & Martelli, 1999; U.S. Pat. No. 5,806,529). Depletion of T cells, however, significantly reduces engraftment success and eliminates the GVL effect.

Alternative strategies have been proposed such as treating the subjects undergoing bone marrow transplantation with immunosuppressive regimens, to avoid GVHD. However, such immunosuppressive treatments are not specific and cause a general and negative immunosuppression in patients.

Patent application US20020127208 discloses a method of transplanting hematopoietic cells from an allogeneic donor comprising the administration of mononuclear cells, including NK cells, which are treated so as to substantially reduce their ability to cause GVHD while they retain their ability to proliferate in the recipient. More particularly, the cells are treated with a chemotherapeutic agent which decreases the biological activity of the mononuclear cells. Similarly, U.S. Pat. No. 5,800,539 discloses a method of transplanting hematopoietic cells from an allogeneic donor comprising the administration of mononuclear cells which are treated so as to render them incapable of proliferating and causing a GVHD. These two documents thus disclose pre-treatment of the graft to reduce the activity of mononuclear cells, suggesting that these cells, including the Natural Killer ("NK") cells have the ability to cause GVHD.

SUMMARY OF THE INVENTION

The present invention discloses novel approaches to enhance the efficacy and safety of allogeneic grafts. These approach are specific, do not cause a general immunosspression in a subject, and allow a very significant reduction of GVHD in human patients.

More specifically, the invention discloses methods of allogeneic transplantations in human subjects in which alloreactive human NK cells are co-administered to the patient. As demonstrated by the inventors in human subjects, the administration of active alloreactive NK cells obviates the need for high-intensity conditioning and drastically reduces GVHD. Moreover, in the presence of active alloreactive NK cells, high numbers of T cells can be grafted, leading to a significantly reduced infection-related morbidity and mortality that are associated with extensive T cell depletion. Therefore, the invention provides a powerful approach for enhancing the efficacy and safety of allogeneic hematopoietic transplantation.

In a particular aspect, the invention concerns a method of transplanting allogeneic graft, more particularly hematopoietic graft, into a human subject in need thereof comprising:
  a) administering to said recipient active alloreactive donor-vs-recipient human natural killer cells; and,
  b) transplanting the allogeneic graft into the recipient.

The invention also relates to methods of reducing GVHD, decreasing the intensity of the conditioning regimen, treating a subject having hematologic disorder, more particularly leukemia, treating or preventing an infection in a recipient undergoing allogeneic graft, enhancing immune reconstitution in a subject undergoing allogeneic graft, for proceeding a hematopoietic graft with a greater T cell content, for increasing the engraftment, for reducing the graft rejection, for avoiding the tumor relapse and/or for conditioning a patient in need of a hematopoietic graft.

The invention also concerns a composition comprising activate alloreactive donor-vs-recipient human natural killer cells and the use of thereof.

LEGEND TO THE FIGURES

FIG. 1. A single infusion of alloreactive NK cells eradicates advanced human leukemia in NOD/SCID mice. Bone marrow infiltration by chronic myeloid leukemia (CML) myeloid blastic crisis, as evaluated by flow cytometric analysis of human CD45 (A), and by polymerase chain reaction analysis of the BCR/ABL gene (B), before (no NK) and 1 week after the infusion of human nonalloreactive NK clones (nonallo-NK) or alloreactive NK clones (allo NK) at the indicated cell doses (data are representative of five mice in each group). In (A), "control" denotes mice not given human leukemia. (C) Survival of leukemic mice that received no alloreactive NK cells (solid squares), $8 \times 10^6$ nonalloreactive NK cells (open squares), or $8 \times 10^5$ alloreactive NK cells (solid triangle) (data are from 10 mice in each group). Identical results were obtained from four additional experiments with cells from three AML patients and one CML patient in myeloid blastic crisis.

FIG. 2. Alloreactive NK cells cause immune- and myeloablation but not GVHD. (A) Donor $H-2^{d/b}$ mouse NK cell alloreactivity against $H-2^b$ recipient targets (curves illustrate representative results of five cytotoxicity assays). Donor Ly49A$^+$/G2$^+$ (Ly49C/I$^-$) NK cells, alloreactive against recipient targets (solid triangles), were used for conditioning. Nonalloreactive, Ly49C/I$^+$ (Ly49A$^-$/G2$^-$) cells (solid squares) served as controls. (B) In vivo infusion of alloreactive NK cells does not cause GVHD. The solid triangle represents survival in lethally (9 Gy) irradiated H-2$^b$ mice given H-2$^{d/b}$ bone marrow plus 16×10$^6$ alloreactive H-$_2^{d/b}$ NK cells versus survival of mice (solid squares) given H-2$^d$ bone marrow plus 10$^6$ H-2$^d$ T cells (number of mice in each group=10). (C and D) Mice were given nonlethal TBI (6.5 Gy), nonlethal TBI plus 4×10$^6$ nonalloreactive NK cells (nonallo NK), nonlethal TBI plus 4×10$^6$ alloreactive NK cells (allo NK), or lethal (9 Gy) TBI alone. Alloreactive NK cells ablated bone marrow (C) and spleen (D) granulocytes (black bars) and T cells (white bars) in nonlethally irradiated mice (mean±SD of data from a total of nine mice, three each in three independent experiments).

FIG. 3. Successful MHC haplotype-mismatched transplantation after alloreactive NK cell-based conditioning. (A) Donor H-2$^{d/b}$ chimerism after conditioning H-2b recipients with lethal TBI (9 Gy), nonlethal TBI (7 Gy), nonlethal TBI plus 4×10$^6$ nonalloreactive NK cells (nonallo NK), or decreasing nonlethal TBI doses (7, 6, and 5 Gy) plus 4×10$^6$ alloreactive NK cells. (B) Alloreactive NK cell doses yielding major donor chimerism in transplantation of nonlethally (6.5 Gy) irradiated mice are low, i.e., 2×10$^5$. (C and D) Mismatched transplantation after conditioning with reduced-intensity fludarabine-based regimens (Giralt et al, 2000). Conditioning regimens were fludarabine (180 mg/m$^2$) plus busulfan (8 mg/Kg) (white bars), fludarabine (120 mg/m$^2$) plus melphalan (120 mg/m$^2$) (hatched bars), fludarabine (120 mg/m2) plus 2 Gy TBI (checked bars), or fludarabine (120 mg/m$^2$) plus cyclophosphamide (120 mg/Kg) (black bars). Survival without transplant after any of these schemes was 100%. (C) Donor chimerism of mice receiving the drugs plus 8×10$^5$ alloreactive NK cells. (D) Donor chimerism of mice receiving either the drugs alone or the drugs plus 8×10$^6$ nonalloreactive NK cells [in panels (A) through (D), data are from three independent experiments, each using six mice]. (E) Post-engraftment infusion of alloreactive NK cells converted mixed chimeras to full-donor chimeras. Donor chimerism in transplanted mice conditioned with fludarabine (120 mg/M$^2$) plus 2×10$^5$ alloreactive NK cells (white bar), as determined 6 months after transplant. The black bar shows donor chimerism, determined 6 months after transplant, in another group of mice that received the same conditioning [fludarabine (120 mg/M$^2$) plus 2×10$^5$ alloreactive NK cells], transplant, and a post-engraftment infusion of 8×10$^5$ alloreactive NK cells given 6 weeks after transplant. The hatched bar shows a control group of mice that received the same conditioning, transplant, and an infusion of 8×10$^6$ nonalloreactive NK cells. In all panels in this figure, the bars represent mean percentages±SD of donor chimerism as evaluated by two-color flow cytometric analysis. Identical degrees of donor chimerism were found in granulocytes and lymphocytes in bone marrows and spleens. Granulocyte and lymphocyte values were pooled and are illustrated as a single bar (all experiments were repeated at least three times).

FIG. 4. Conditioning by alloreactive NK cells protects against GVHD by ablating host APCs. (A) Survival of H-2$^b$ mice conditioned with TBI (9 Gy) (solid circles) or TBI plus nonalloreactive NK cells (4×10$^6$) (solid squares), and transplanted with H-2$^d$ bone marrow containing 10$^6$ T cells, versus that of H-2$^b$ mice conditioned with TBI (9 or 6.5 Gy) plus alloreactive NK cells (4×10$^5$) and given H-2$^d$ BMT containing 2×10$^7$ T cells (solid triangle). Survival of H-2$^b$ mice bearing H-2$^{d/b}$ APCs and therefore resistant to alloreactive NK cell killing (H-2$^{d/b\,H-}$2$^b$ chimeras), conditioned with TBI plus alloreactive NK cells and transplanted with H-2$^d$ bone marrow containing 10$^6$ T cells (open squares) versus survival of control H-2$^b$ H-2$^b$ chimeras (with susceptible APCs) conditioned with TBI (9 or 6.5 Gy) plus alloreactive NK cells (4×10$^5$) and given H-2$^d$ BMT containing 2×10$^7$ T cells (same as solid triangle). (B) Bone marrow, (C) spleen, and (D) gut APC (CD11c$^+$ dendritic cell) counts in untreated mice (black bar) versus mice conditioned with 9 Gy TBI with or without 4×10$^6$ nonalloreactive NK cells (the two hatched bars, respectively) versus mice conditioned with either 9 or 6.5 Gy TBI plus 4×10$^5$ alloreactive NK cells (the two white bars, respectively).

DETAILED DESCRIPTION OF THE INVENTION

The present invention relates to improvements in allogeneic grafts in human subjects. The invention more specifically discloses that the use of active NK cells having certain phenotype or properties can significantly increase the efficacy of allogeneic transplantations in human subject, particularly hematopoietic transplantations. Alloreactive NK cells can be successfully combined with reduced-intensity conditioning to achieve durable full-donor engraftment. Even alone, NK cells convert mixed to full-donor chimerism and eradicated leukemia. NK cell conditioning even protects against GVHD efficiently enough to allow the safe infusion of otherwise lethal doses of allogeneic T cells for immune reconstitution.

The invention concerns a method of transplanting allogeneic graft into a human subject in need thereof comprising:
  a) administering to said recipient an effective amount of active alloreactive donor-vs-recipient human natural killer cells; and,
  b) transplanting the allogeneic graft into the recipient.

This method of transplanting allogeneic graft, more particularly hematopoietic graft, can be applied for reducing the GVHD, for decreasing the intensity of the conditioning regimen, for treating a subject having hematologic disorder, more particularly leukemia, for treating or preventing an infection in a recipient of allogeneic graft, for enhancing immune reconstitution in an allogeneic graft recipient, for proceeding a hematopoietic graft with a greater T cell content, for increasing the engraftment, for reducing the graft rejection, for avoiding the tumor relapse and/or for conditioning a patient in need of a hematopoietic graft.

The invention concerns a method of reducing GVHD in a subject of allogeneic graft, preferably bone marrow transplantation, in need thereof comprising:
  a) administering to said subject an effective amount of active alloreactive donor-vs.-recipient human natural killer cells; and
  b) transplanting said allogeneic graft into said subject the administration of said alloreactive NK cells reducing GVHD in said subject.

The invention concerns a method of reducing the intensity of conditioning regimen for a subject in need of an allogeneic graft, preferably an allogeneic hemapoietic cells graft, comprising a) administering to said subject an effective amount of active alloreactive donor-vs-recipient human natural killer cells in combination with the administration of the reduced-intensity conditioning regimen; and, b) transplanting the allogeneic graft into the subject. By "in combination" is intended that the natural killer cells can be administered to the subject before, simultaneously with or, after the administration of the reduced-intensity conditioning regimen. Preferably, said reduced-intensity conditioning regimen is the conditioning regimen adopted for matched human transplants.

The invention concerns a method of treating a subject having hematologic disorder comprising transplanting a allogeneic graft into said subject so as to treat said disorder, the improvement comprising administering to said subject an effective amount of active alloreactive donor-vs.-recipient human natural killer cells.

Hematologic disorder includes neoplastic proliferation of hematopoietic cells. Optionally, said hematologic disorder is selected from the group consisting of lymphoblastic leukemia, acute or chronic myelogenous leukemia, Hodgkin's lymphoma, Non-Hodgkin's lymphoma, myelodysplastic syndrome, multiple myeloma, and chronic lymphocytic leukemia. Preferably said hematologic disorder is a leukemia, more preferably myeloid leukemia. Hematologic disorder also includes non-malignant disorders such as an inherited erythrocyte abnormalities, an inherited immune system disorders or a hemoglobinopathy, e.g. sickle cell anemia, aplastic anemia or thalassemia.

The present invention concerns a method of treating or preventing an infection in a subject of allogeneic graft comprising: a) administering to said subject an effective amount of active alloreactive donor-vs-recipient human natural killer cells; and, b) transplanting into said subject said allogeneic graft, said graft comprising T cells which are effective in treating or preventing said infection.

The invention also concerns a method of enhancing immune reconstitution in an allogeneic graft recipient comprising: a) administering to the subject an effective amount of active alloreactive donor-vs-recipient human natural killer cells; and, b) transplanting into the subject the allogeneic graft comprising allogeneic T cells which are effective for the immune reconstitution.

The invention further concerns a method of increasing the engraftment and/or for reducing the graft rejection comprising: a) administering to said subject an effective amount of active alloreactive donor-vs-recipient human natural killer cells; and, b) transplanting into the subject the allogeneic graft, the active alloreactive human NK cells causing increased engraftment or decreased graft rejection.

In one embodiment of the methods according to the present invention, the natural killer cells and allogeneic graft are administered simultaneously. In an alternative embodiment, the natural killer cells are administered prior to the allogeneic graft. Preferably, said allogeneic graft is a hematopoietic graft. Optionally, said hematopoietic graft is a bone marrow transplant. In a particularly interesting embodiment of the methods according to the present invention, said recipient or subject is treated for leukemia, more preferably myeloid leukemia, optionally an acute or chronic myeloid leukemia. Optionally, the allogeneic graft has an increased content of allogeneic T cells. Preferably, said subject is treated under myelo-reductive regimen before the transplantation of the allogeneic graft, optionally myelo-ablative regimen. Preferably, said active alloreactive natural killer cells comprise at least 5% of alloreactive NK cells against the recipient cells among its NK cells content, preferably at least 20 or 30%, more preferably at least 40 or 50%, still more preferably at least 60, 70 or 90%. Optionally essentially all the NK cells are allorective against the recipient cells.

The invention contemplates a method of avoiding the tumor relapse in a subject comprising administering to the subject an effective amount of active alloreactive donor-vs-recipient human natural killer cells, which are effective against the tumor relapse in combination transplanting the allogeneic graft into the subject.

Additionally, the invention concerns a method of conditioning a subject in need of an allogeneic graft, preferably a hematopoietic graft, comprising administering to the subject an effective amount of active alloreactive donor-vs-recipient human natural killer cells before or simultaneously with the allogeneic graft. Preferably, said effective amount of active alloreactive donor-vs-recipient human natural killer cells are administered in combination with a conditioning regimen, preferably a reduced-intensity regimen.

The invention concerns a composition comprising active alloreactive donor-vs-recipient human natural killer cells, the use of said composition for reducing the GVHD, for decreasing the intensity of the conditioning regimen, for treating a subject having hematologic disorder, more particularly leukemia, for treating or preventing an infection in a recipient of allogeneic graft, for enhancing immune reconstitution in an allogeneic graft recipient, for proceeding a hematopoietic graft with a greater T cell content, for increasing the engraftment, for reducing the graft rejection, for avoiding the tumor relapse and/or for conditioning a patient in need of a hematopoietic graft. In a preferred embodiment, said composition does not comprise IL-2. Preferably, said composition is enriched in alloreactive natural killer cells regarding to the non-alloreactive natural killer cells content. Said composition comprises at least 5% of alloreactive NK cells among its NK cells content, preferably at least 20 or 30%, more preferably at least 40 or 50%, still more preferably at least 60, 70 or 90%. Optionally essentially all the NK cells comprised in said composition are allorective against the recipient cells.

As used herein, "hematopoietic cells" means a population of human cells that possesses the capability of dividing and producing progeny that include all of the formed cellular elements of the blood. As used herein, "donor" means the human that is the natural source from which the graft, preferably hematopoietic cells, are originally removed. Also as used herein, a "recipient" is the human into which the graft, preferably hematopoietic cells, will be transplanted. The term "allogeneic" as used herein means that the recipient is not the natural source from which the graft, preferably hematopoietic cells, have been removed. Major histocompatability complex antigens (also called human leukocyte antigens, HLA) are protein molecules expressed on the surface of cells that confer a unique antigenic identity to these cells. MHC/HLA antigens are target molecules that are recognized by certain immune effector cells (T-cells and natural killer (NK) cells) as being derived from the same source of hematopoietic reconstituting stem cells as the immune effector cells ("self") or as being derived from another source of hematopoictic reconstituting cells ("non-self"). By "GVHD" is intended graft versus host disease. By "GVL" is intended graft versus leukemia. By "subject" or "recipient" is intended a human being.

Natural killer (NK) cells are a sub-population of lymphocytes, involved in non-conventional immunity. NK cells can be obtained by various techniques known in the art, such as from blood samples, cytapheresis, collections, etc. NK cells are negatively regulated by major histocompatibility complex (MHC) class I-specific inhibitory receptors (Kärre et al., 1986; Öhlén et al, 1989). In humans, receptors termed killer Ig-like receptors (KIRs) recognize groups of HLA class I alleles. Although KIRs and other class-I inhibitory receptors (Moretta et al, 1997; Valiante et al, 1997a; Lanier, 1998) may be co-expressed by NK cells, in any given individual's NK repertoire there are cells that express a single KIR and are blocked only by a specific class I allele group. Missing expression of the KIR ligand on mismatched allogeneic cells can therefore trigger NK cell alloreactivity (Ciccone et al, 1992a, 1992b; Colonna et al, 1993a, 1993b; Bellone et al, 1993; Valiante et al, 1997b). During hematopoietic transplants, when the recipient's class I alleles do not block all donor NK cells, donor alloreactive NK clones can be generated (Ruggeri et al, 1999).

Characteristics and biological properties of NK cells include the expression of surface antigens including CD16, CD56 and/or CD57, and the absence of the alpha/beta or gamma/delta TCR complex expressed on the cell surface; the ability to bind to and kill cells that fail to express "self" MHC/HLA antigens by the activation of specific cytolytic enzymes; the ability to kill tumor cells providing that tumor cells express a NKR-ligand; the ability to release protein molecules called cytokines that stimulate or inhibit the immune response; and the ability to undergo multiple rounds of cell division and produce daughter cells with similar biologic properties as the parent cell. Properties of monocytes include the ability to engulf bacteria and "non-self" cells (phagocytosis); the elaboration of cytokines that stimulate T cells and NK cells; the release of molecules that cause inflammation; and the presentation of antigens to T cells. By "active" NK cell is intended fully biologically active NK cells, more particularly NK cells having the capacity of lysing target cells. More particularly, "active" NK cells refer to an ex vivo cultures or expanded NK cell population, more preferably a NK cell population treated or cultured in vitro or ex vivo in the presence of a cytokine such as an interleukin, more preferably IL-2. For instance, an "active" NK cell is able to kill cells that express a NKR-ligand and fail to express "self" MHC/HLA antigens (KIR-incompatible cells).

Inhibition of natural killer (NK) cell lysis is signaled through specific receptors which bind to polymorphic determinants of major histocompatibility complex (MHC) class I molecules or HLA. Some receptors are a family of Ig-like molecules known as killer cell inhibitory receptors (KIR).

As used herein, alloreactive NK cells refer to NK cells which do not express a KIR (killer cell inhibitory receptor) able to bind a MHC/HLA antigen of the recipient (a KIR incompatibility in the donor-vs-recipient direction). More particular, said alloreactive NK cells are not able to bind one of the HLA-A, HLA-B or HLA-C antigen in the host, preferably the HLA-B or HLA-C antigen. The KIRs with two Ig domains (KIR2D) identify HLA-C allotypes: KIR2DL2 (formerly designated p58.1) or the closely related gene product KIR2DL3 recognizes an epitope shared by group 1 HLA-C allotypes (Cw2, 4, 5, and 6), whereas KIR2DL1 (p58.2) recognizes an epitope shared by the reciprocal group 2 HLA-C allotypes (Cw1, 3, 7, and 8). One KIR with three Ig domains KIR3DL1 (p70) recognizes an epitope shared by HLA-Bw4 alleles. Finally, a homodimer of molecules with three Ig domains KIR3DL2 (p140) recognizes HLA-A3 and -A11.

The most interesting KIRs identify HLA-C allotypes. Indeed, only two KIRs, namely KIR2DL2 or KIR2DL3, and KIR2DL1, are sufficient for covering all the HLA-C allotypes, respectively group 1 HLA-C allotypes and group 2 HLA-C allotypes.

KIR genes, each expressed by some of the individual's NK cells, vary considerably among individuals. It is believed that during development each NK cell precursor makes a random choice of which KIR genes it will express, and the different combinations of HLA class I molecules select NK cells that express receptors for self HLA class I. Consequently, the NK cells from any given individual will be alloreactive toward cells from others which lack their KIR ligands and, conversely, will be tolerant of cells from another individual who has the same or additional KIR ligands.

Therefore, the alloreactive NK cells are derived from a donor, more particularly an alloreactive donor, selected for having mismatch with the recipient for at least one antigen of the three major HLAs, preferably those of the HLA-C and HLA-B. For example, if the recipient presents a group 1 HLA-C allotype, the donor has a group 2 HLA-C allotype. Reciprocally, for a recipient having a group 2 HLA-C allotype, the donor is selected such that it presents a group 1 HLA-C allotype. In an additional example, for a recipient having a group Bw4 HLA-B allotype, the donor is selected such that it does not present a group Bw4 HLA-B allotype. Reciprocally, for a recipient who has not a group Bw4 HLA-B allotype, the donor is selected such that it presents a group Bw4 HLA-B allotype.

Remarkably, when donor-recipient haplo-mismatched pairs were also KIR ligand mismatched (as in this example), 100% of the donors tested had (at least some) alloreactive NK cells in their repertoires. Therefore, in a population of NK cells from an alloreactive donor, 5-50% of NK cells are alloreactive.

The alloreactive NK cells are prepared from a donor by different techniques which are known by the skilled person. More particularly, these cells can be obtained by different isolation and enrichment methods using peripheral blood mononuclear cells (lymphoprep, leucapheresis, etc . . . ). These cells can be prepared by Percoll density gradients (Timonen et al., 1982), by negative depletion methods (Zarling et al., 1981) or by FACS sorting methods (Lanier et al., 1983). These cells can also be isolated by column immunoadsorption using an avidine-biotin system (Handgretinger et al., 1994) or by immunoselection using microbeads grafted with antibodies (Geiselhart et al., 1996-97). It is also possible to use combinations of these different techniques, optionally combined with plastic adherence methods. For example, the alloreactive NK cells can be prepared by providing blood mononuclear cells depleted of T cells from the donor, activating said cells with phytohemagglutinin (PHA) and culturing said cells with interleukin (IL)-2 and irradiated feeder cells. Optionally, the population of NK cells can be tested for the alloreactivity against the recipient cells. Optionally, said NK cells can be cloned and each clone is tested for the alloreactivity against the recipient cells. Optionally, the NK cell clones presenting the alloreactivity are pooled. The alloreactivity is tested by standard 51 Cr release cytotoxicity against recipient PHA lymphoblasts, or Epstein-Barr virus transformed B lymphoblastoid cell lines.

Therefore, the alloreactive NK cells according to the present invention can be prepared by a method comprising: a) providing NK cells from an alloreactive donor; b) activating said NK cells with IL-2; c) collecting the active NK cells resulting from step b). Optionally, said method comprises an additional step of testing the alloreactivity of the NK cells collected from step c) against the recipient cells. Alternatively, the alloreactive NK cells according to the present invention can be prepared by a method comprising: a) providing NK cells from an alloreactive donor; b) isolating or cloning said NK cells; c) activating said NK cells with IL-2; d) testing the alloreactivity of the NK cells resulting from step c) against the recipient cells; and, optionally, e) pooling the alloreactive NK cells. NK cells can be further expanded in vivo or in vitro.

In a first embodiment, said alloreactive NK cells contain essentially only alloreactive NK cells. In an alternative embodiment, said alloreactive NK cells refers to a population of NK cells prepared from an alloreactive donor. In this case, said population comprises both alloreactive and non-alloreactive NK cells. Preferably, this NK cells population comprises at least 5% of alloreactive NK cells, more preferably at least 20% of alloreactive NK cells, still more preferably at least 30% of alloreactive NK cells.

The graft, preferably hematopoietic cells, and the alloreactive NK cells can be from the same donor source or they can be from different donors. If different donors are used, such donors are preferably non-alloreactive for one to the other. Hence, they are HLA compatible. These donor source cells which are propagated in vitro or derived in vitro from a less differentiated cell type of the donor source, for example, from a yolk sac or other embryonic fetal tissue source such as embryonic stem cells.

According to the methods and compositions of the present invention, active alloreactive NK cells and hematopoietic cells are administered in an efficient amount.

The efficient amount of alloreactive NK cells administered to the recipient can be between about $0.05 \times 10^6$ and about $100 \times 10^6$ cells/kg of recipient's body weight. Subranges of pure alloreactive NK cells are also provided, for example, about $0.05 \times 10^6$ to $5 \times 10^6$ cells/kg of recipient's body weight, about $5 \times 10^6$ to $10 \times 10^6$ cells/kg of recipient's body weight, about $10 \times 10^6$ to $50 \times 10^6$ cells/kg of recipient's body weight, about $50 \times 10^6$ to $100 \times 10^6$ cells/kg of recipient's body weight. Preferably, the amount of alloreactive NK cells administered to the recipient is comprised between $5 \times 10^6$ to $15 \times 10^6$ cells/kg of recipient's body weight.

The efficient amount of hematopoietic cells administered to the recipient can be between about $0.2 \times 10^6$ and about $10 \times 10^8$ CD34+ cells/kg of recipient's body weight, preferably between about $0.1 \times 10^6$ and about $20 \times 10^6$ CD34+ cells/kg of recipient's body weight, more preferably about $10 \times 10^6$ CD34+ cells/kg of recipient's body weight. In a preferred embodiment, the graft comprises a maximum of $1 \times 10^5$ CD3+ cells/kg of recipient's body weight, more preferably a maximum of $1 \times 10^4$ CD3+ cells/kg of recipient's body weight.

The alloreactive NK cells and hematopoietic cells are typically administered to the recipient in a pharmaceutically acceptable carrier by intravenous infusion. Carriers for these cells can include but are not limited to solutions of phosphate buffered saline (PBS) containing a mixture of salts in physiologic concentrations.

Contrary to the disclosure of the article (Asai et al., 1998), the administration of active NK cells without any IL-2 is enough to increase the engraftment and to protect against GVHD.

The hematopoietic cells can be provided by bone marrow cells, mobilized peripheral blood cells or cord blood cells. The bone marrow cells can be obtained from the donor by standard done marrow aspiration techniques know in the art, for example by aspiration of marrow from the iliac crest.

Peripheral blood stem cells are obtained after stimulation of the donor with a single or several doses of a suitable cytokine, such as granulocyte colony-stimulating factor (G-CSF), granulocyte/macrophage colong-stimulating factor (GM-CSF) and interleukin-3 (IL-3). In a preferred embodiment of the invention, the donor is stimulated with G-CSF (Caspar et al., 1993). In order to harvest desirable amounts of stem cells from the peripheral blood cells, leukapheresis is performed by conventional techniques (Caspar et al., 1993) and the final product is tested for mononuclear cells.

The hematopoictic cells can be enriched from the source population by selecting cells that express the CD34 antigen, using combinations of density centrifugation, immuno-magnetic bead purification, affinity chromatography, and fluorescent active cell sorting (FACS), known to those skilled in the art (Baum, et al., 1992; Lansdorp, et al., 1990; Sato, et al., 1991; Smith, et al., 1991; Udomsakdi, et al., 1991; Udomsakdi, et al., 1992).

Optionally, the hematopoietic cells can be T-cell depleted. T-cell depletion of bone marrow or of peripheral blood cell may be carried out by any known technique (Blazer et al., 1985), for example, by soybean agglutination and E-rosetting with sheep red blood cells as described (Reisner et al., 1981, 1986).

However, in a preferred embodiment of the invention, the T cells are not depleted from the obtained hematopoietic cells. Indeed, the administration of active alloreactive NK cells replaces the need of T-cell depletion. The T-cell content of the graft can also be increased and consequently reduces the infection-related morbidity andmortality that are associated with the extensive T-cell depletion.

The natural killer cells and allogeneic graft can be administered simultaneously. Alternatively, the natural killer cells and the allogeneic graft are administered sequentially. If a VGHD effect is desired, the NK cells are not administered to the subject after the allogeneic graft. However, if a VGL effect is desired, the NK cells can be administered at any moment. Similarly, if a convertion of mixed to full-donor chimerism is wished for, the NK cells can be administered at any moment.

Preferably, the active alloreactive NK cells are administered up to 15 days prior to administration of the allogeneic graft. Preferably, the NK cells are administered between 10 and 2 days, more preferably about 2 days.

According to the invention the host patient is conditioned prior to the transplantation of the allogeneic graft. Conditioning may be carried out under sublethal, lethal or supralethal conditions, for example by total body irradiation (TBI) and/or by treatment with myelo-reductive or myelo-ablative and immunosuppressive agents. According to standard protocols, a lethal dose of irradiation is within the range of 7-9, 5 Gy TBI, a sublethal dose is within the range of 3-7 Gy TBI and a supralethal dose is within the range of 9, 5-16 Gy TBI.

Any immunosuppressive agent used in transplantation to control the rejection, or a combination of such agents, can be used according to the invention, such as prednisone, methyl prednisolone, azathioprine, cyclophosphamide, cyclosporine, monoclonal antibodies against T-cells, e.g. OKT3, and antisera to human lymphocytes (antilymphocyte globulin—ALS) or to thymus cells (antithymocyte globulin—ATG). Examples of myelo-ablative agents that can be used according to the invention are busulphan, dimethyl myleran and thiotepa.

The advantage of the administration of active alloreactive NK cells is the possibility to reduce the intensity of the conditioning regimen. For example, the conditioning regimen can be reduced to the intensity conditioning regimen adopted for matched human transplants. A reduced version of a highl-intensity regimen according to the present invention includes Fludarabine at the total dose of 200 mg/M$^2$, Thiotepa 5 mg/Kg, and Melphalan 70 mg/M$^2$, plus anti-T cell antibodies such as ATG, 20 mg/Kg. Optionally, the doses of Thiotepa and Melphalan can be increased by 50%. Indeed, such conditioning regimen is highly toxic and some patients are unable to withstand such toxicity. Therefore, the present invention makes possible the allogeneic graft for these patients.

EXAMPLES

In clinical transplantation and in mouse transplant models, we determined the impact of donor-versus-recipient NK cell alloreactivity on relapse, rejection, GVHD, and survival. One hundred and twelve high-risk acute leukemia patients received hematopoietic transplants from HLA haplotype-mismatched family donors (Martelli et al, 2002; Aversa et al, 1994, 1998). Typing of the HLA-C locus was available in 92 of these individuals [of whom 57 had AML and 35 had acute lymphoid leukemia (ALL)], and so only these transplants were analyzed in this study. HLA was assessed by serologic and molecular typing. All transplant pairs were mismatched at the HLA-A, -B, -C, and DR loci of one haplotype and matched at the other. Primary engraftment was achieved in 90.2%, GVHD occurred in 8.6%, and event-free survival was seen in 26% of AML patients and 8% of ALL patients. "Event free" denotes survival without rejection, chronic GVHD, leukemia relapse, or infection. All patients had a minimum follow-up of 1 year and were evenly distributed across the 1- to 8-year follow-up range.

To evaluate the role of donor-versus-recipient NK cell alloreactivity in transplantation outcomes, donor-recipient pairs were divided into two groups: the first without and the second with KIR ligand incompatibility in the graft-versus-host (GVH) direction (Table 1). Donors were evaluated for NK cell alloreactivity by screening 200 NK clones (100 on each of two separate occasions) and were scored positive when the frequency of lytic clones was 1 in 50 [as a rule, frequencies of positive clones were either high (1 in 2 to 1 in 20) or nondetectable (<1 in 200)]. KIR ligand incompatibility correlated closely with the detection of donor NK clones killing recipient targets. Transplantation from NK cell alloreactive donors totally protected patients against rejection, GVHD, and AML relapse (Table 1). In AML, the probability of event-free survival at 5 years was 5% in the first group versus 60% in the second (P<0.0005). Multivariate analysis that considered crucial variables affecting transplantation outcome, such as conditioning regimens, number of stem cells and T cells in the graft, and status of disease at transplant, showed that KIR ligand incompatibility in the GVH direction was the only independent predictor of survival in AML. Conversely, the absence of KIR ligand incompatibility in the GVH direction was the only independent factor predicting poor outcome (hazard ratio=0.33, 95% confidence interval 0.11 to 0.94, P<0.04). KIR ligand incompatibility in the GVH direction had no effect on ALL. In human transplants, we showed that donor-versus-recipient natural killer (NK)-cell alloreactivity could eliminate leukemia relapse and graft rejection and protect patients against GVHD.

Table 1. Clinical data and transplantation outcomes in HLA haplotype-mismatched transplants with and without KIR ligand incompatibility in the GVH direction. KIR ligand incompatibility in the GVH direction was defined as absence in recipients of donor class I allele group(s) recognized by KIRs (Moretta et al, 1997; Valiante et al, 1997a; Lanier, 1998). Such groups are HLA-C alleles with $Asn^{77}$-$Lys^{80}$, Cw2, 4, 5, 6, and related alleles; HLA-C alleles with $Ser^{77}$-$Asn^{80}$, Cw1, 3, 7, 8, and related alleles; HLA-Bw4 alleles; and HLA-A3/A11. Twenty-six pairs (11 in ALL and 15 in AML) were mismatched for HLA-C groups, 8 (3 in ALL, and 5 in AML) were mismatched for HLA-Bw4 group; the HLA-A3/A11 mismatch was never found alone but only in conjunction with HLA-C group mismatches (2 pairs).

| KIR ligand incompatibility in GVH direction Number of transplants | No 58 | Yes 34 |
|---|---|---|
| Donors displaying antirecipient NK clones | 1/58 | 34/34* |
| Disease | | |
| ALL | 21 | 14 |
| AML | 37 | 20 |
| Transplantation outcomes | | |
| Rejection | 15.5% | 0%* |
| Acute GVHD, grade II | 13.7% | 0%* |
| Probability of relapse at 5 years | | |
| ALL | 90% | 85% |
| AML | 75% | 0%** |

P 0.01-** P < 0.0008 (22).

Figure 1A:
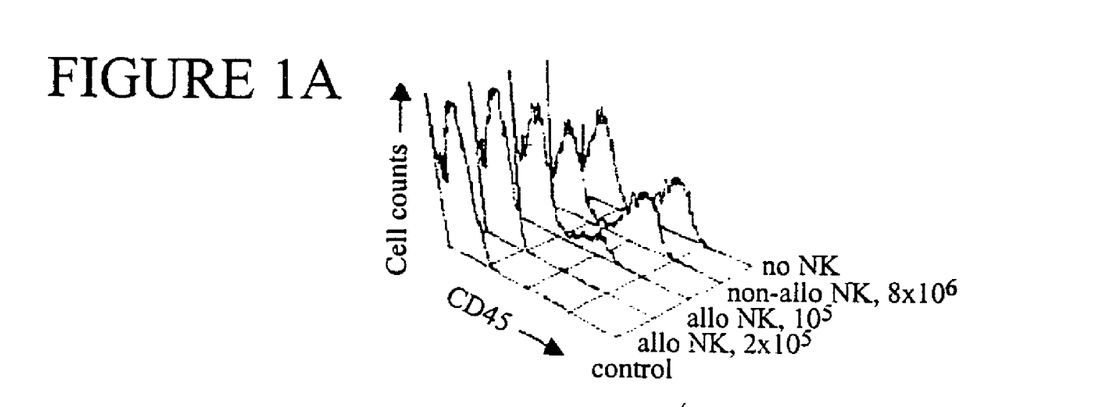
Figure 1B:
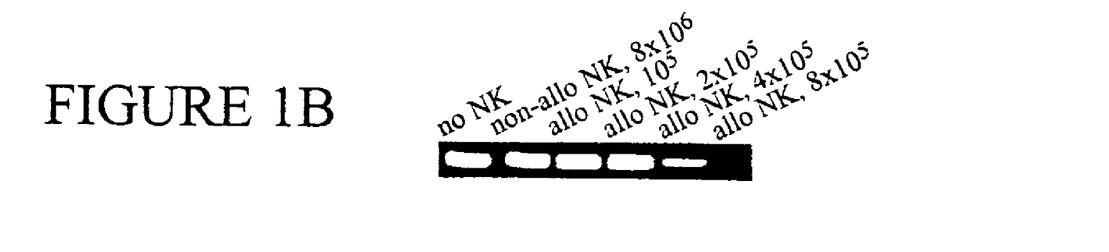
Figure 1C:
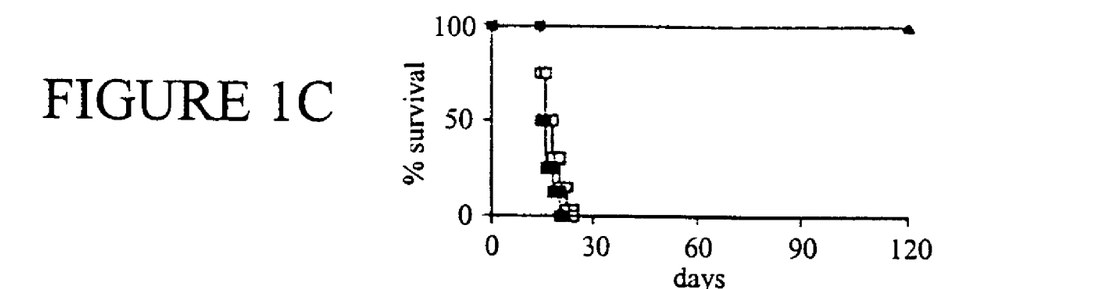

Our data on the human system suggested that alloreactive NK cells are responsible for GVL effects. In light of these observations, we explored these effects in a model system, using transfer of alloreactive NK cells. In these experiments, human alloreactive NK clones were infused into human AML-engrafted nonobese diabetic/severe combined immunodeficient (NOD/SCID) mice. Mice infused with human AML developed advanced disease in 5 to 6 weeks (FIG. 1, A and B). If left untreated, or given nonalloreactive human NK clones, mice died over the following 3 weeks (FIG. 1, C). In contrast, many fewer human alloreactive NK cells cleared leukemia (FIG. 1, A and B), and mice survived until they were killed (120 days) (FIG. 1, C).

Figure 2A:
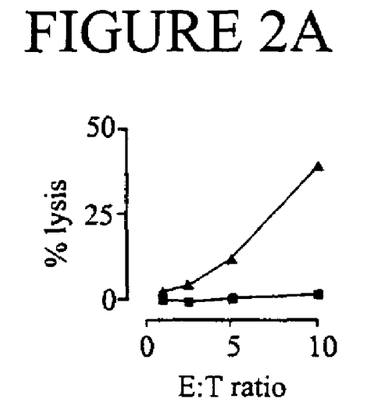
Figure 2B:
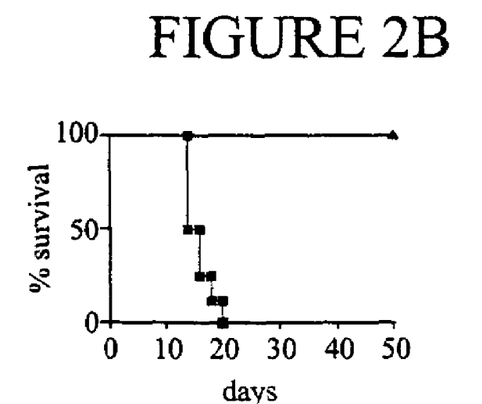
Figure 2C:
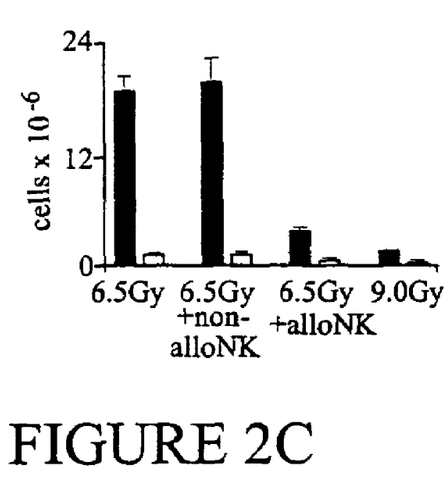
Figure 2D:
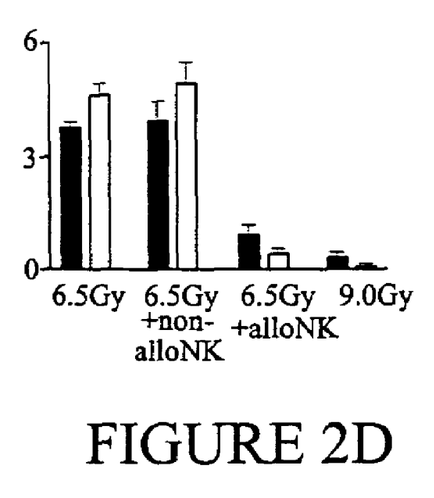

We next tested whether alloreactive NK cells could obviate the need for lethal conditioning in an MHC mismatched $F_1$ parent mouse bone marrow transplant (BMT) model. In $F_1$ $H\text{-}2^{d/b}$ parent $H\text{-}2^b$ transplants, donor T cells were tolerant of the recipient MHC, but donor NK cells not expressing $H\text{-}2^b$-specific Ly49C/I inhibitory receptor and bearing instead $H\text{-}2^d$ specific Ly49A/G2 receptors were activated to kill the recipient's targets (FIG. 2A) (21,23). Alloreactive NK cells did not cause GVHD, even when infused in large numbers into lethally irradiated recipients (FIG. 2B). However, in nonlethally irradiated recipients, alloreactive NK cells but not control nonalloreactive NK cells reduced recipient-type T cell and granulocyte counts in marrow and spleen to levels observed after lethal irradiation (FIG. 2, C and D).

Figure 3A:
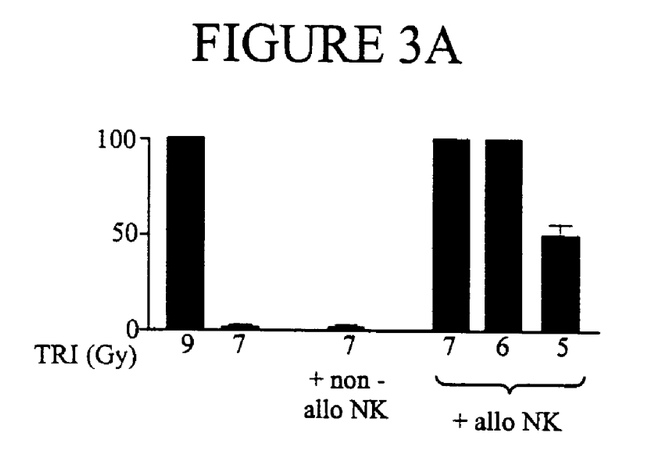
Figure 3B:
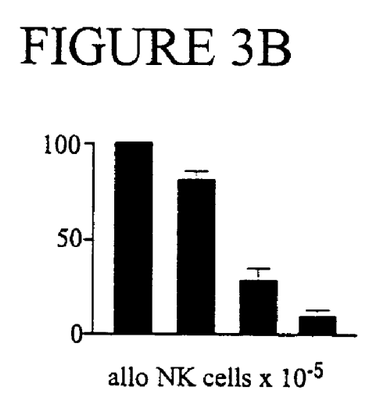
Figure 3C:
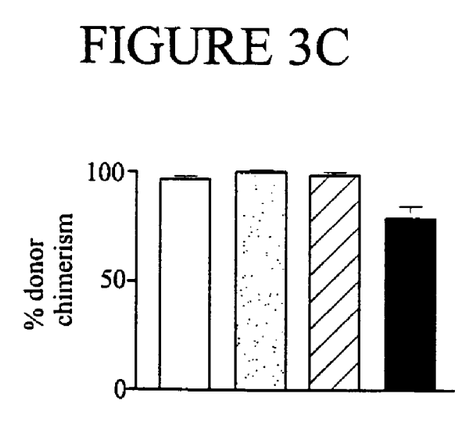
Figure 3D:
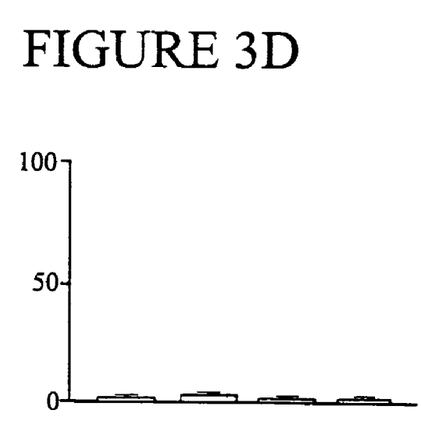
Figure 3E:
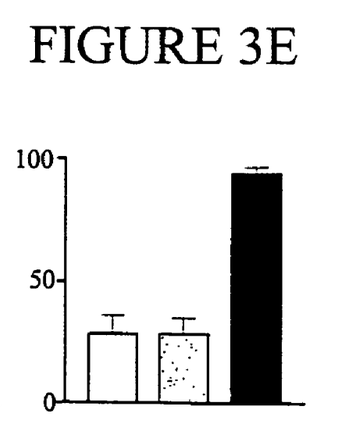
Figure 4A:
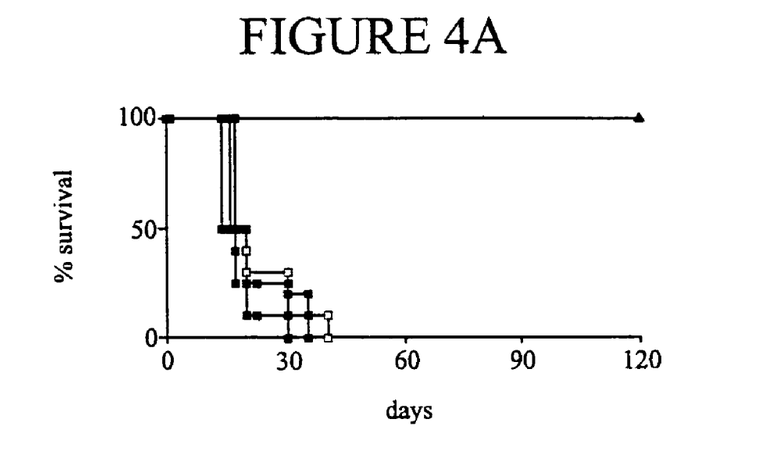
Figure 4B:
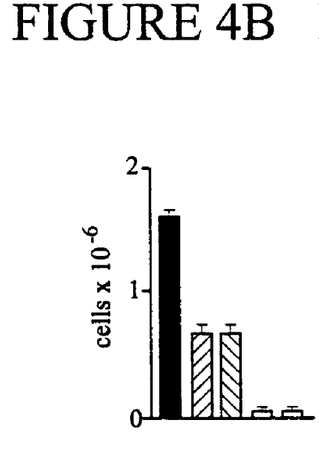
Figure 4C:
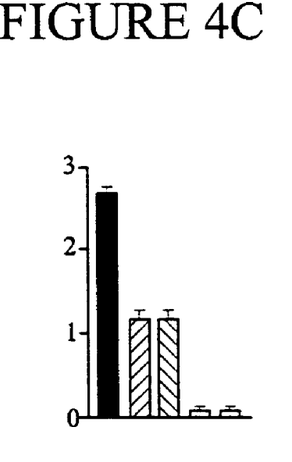
Figure 4D:
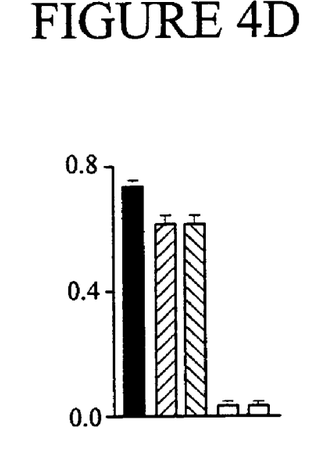

Mice conditioned with nonlethal [7 grays (Gy)] total-body irradiation (TBI) alone rejected donor marrow grafts (FIG. 3A). In contrast, all recipients conditioned with nonlethal irradiation and alloreactive NK cells engrafted with durable, donor-type hematopoietic chimerism (FIG. 3A). As few as $2\times10^5$ alloreactive NK cells resulted in major donor hematopoiesis, and $4\times10^6$ nonalloreactive NK cells had no effect (FIG. 3B). Similar results were obtained in $F_1$ $H\text{-}2^{d/b}$ parent $H\text{-}2^d$ transplants. In this case, donor NK cells used for conditioning did not express H-2 specific Ly49A/G2 receptors but expressed instead the $H\text{-}2^b$-specific Ly49C/I receptor. Alloreactive NK cells allowed mismatched BMT, even when combined with the reduced-intensity conditioning regimens adopted from matched human transplants (Giralt et al, 2000). Thus, mice given these regimens plus low doses of alloreactive NK cells achieved>80% donor chimerism (FIG. 3C), unlike controls that received nonalloreactive NK cells. Even mice conditioned with fludarabine alone plus alloreactive NK cells displayed 30% donor chimerism (FIG. 3E). In addition, infusion of alloreactive NK cells 6 weeks after transplant was able to convert mixed chimeras to stable full-donor chimerism. Because our clinical data suggested that NK cell alloreactivity does not cause GVHD but actually protects against it, we next tested whether NK cell conditioning could replace the need for T cell depletion. Lethally irradiated $H\text{-}2^b$ mice transplanted with $H\text{-}2^d$ bone marrow containing $10^6$ T cells died from GVHD in 2 to 4 weeks (FIG. 4A). After conditioning with TBI plus alloreactive NK cells, cohorts of transplanted mice were given escalating doses of $H\text{-}2^d$ T cells. Even with as many as $2\times10^7$ T cells, 100% of these mice survived until they were killed (120 days) with no signs of GVHD. In contrast, administration of nonalloreactive NK cells, even in very large numbers, provided no protection. We hypothesized that this protection might be mediated by alloreactive NK cells attacking recipient antigen-presenting cells (APCs), shown to be responsible for initiating GVHD (Hosaka et al, 1992; Slomchik et al, 1999), and that consequently, mice with APCs that are resistant to alloreactive NK cell killing might not be protected against GVHD. We therefore made B6×BALB/c B6 bone marrow chimeras to replace the alloreactive NK cell-sensitive H-$2^b$ mouse hematopoietic cells, including APCs, with H-$2^{d/b}$ cells that would be resistant to NK cell killing (H-$2^{d/b}$ H-$2^b$ chimeras). Although the H-$2^d$ allele protects against alloreactive NK cells, the H-$2^b$ molecules can still present antigen to donor H-$2^d$ T cells, thus priming GVH reactions. When analyzed 4 months after transplant, >90% of bone marrow, spleen, and gut dendritic cells in these chimeras were of H-$2^{d/b}$ origin. When these chimeras were reconditioned with TBI plus alloreactive NK cells and reconstituted with H-$2^d$ BMT containing $10^6$ T cells, 100% died from GVHD (FIG. 4A). Control H-$2^b$ H-$2^b$ chimeras given $2 \times 10^7$ T cells survived with no signs of GVHD. We also found that alloreactive NK cells accelerated the loss of bone marrow, spleen, and gut APCs, as compared to mice conditioned with either TBI or TBI plus nonalloreactive NK cells (FIG. 4, B, through D). Taken together, these data indicate that alloreactive NK cells prevent GVHD by elimination of recipient APCs.

Our clinical data show that spontaneously generated NK cell alloreactions from stem cell grafts are associated with a remarkable GVL effect and total control of rejection and GVHD. This dramatically affects survival of AML patients (5% in the absence versus 60% in the presence of NK cell alloreactivity). This is far better than survival after matched unrelated-donor transplant, which is 34% in first complete remission, 27% in second complete remission, and 7% in third or more complete remission or in relapse (Stockerl-Goldstein et al, 1999). This survival rate is striking, as most of our AML patients were in their third or more complete remission or in relapse.

Direct involvement of NK cell alloreactivity is provided by our transplant models, which demonstrate that infusion of alloreactive NK cells eradicates human leukemia in vivo, prepares mice for MHC-mismatched BMT by killing host lymphohematopoietic cells, and reduces GVHD by eliminating recipient-type APCs. In humans as in mice, NK cells had no effect unless the target was susceptible to alloreactive NK cell killing; for instance, they failed to control ALL, a leukemia histotype that is resistant to alloreactive NK lysis in vitro (Ruggeri et al, 1999).

Alloreactive NK cell infusions have the potential to improve outcomes of KIR ligand-mismatched transplants even further and are therefore of extraordinary therapeutic interest. In mice, they were successfully combined with reduced-intensity conditioning to achieve durable full-donor engraftment. Even alone, alloreactive NK cells converted mixed to full-donor chimerism and eradicated leukemia. NK cell conditioning even protected against GVHD efficiently enough to allow the safe infusion of otherwise lethal doses of allogeneic T cells for immune reconstitution.

Alloreactive NK cells emerge as a form of cell therapy that might be used in conditioning regimens for host immune suppression and leukemia ablation. Their ability to prevent GVHD could allow a greater T cell content in the graft and consequently reduce the infection-related morbidity and mortality that are associated with extensive T cell depletion (Aversa et al, 1994; 1998). With this approach, mismatched transplants can be envisaged for the elderly and for heavily pretreated patients.

Supplemental Table 1. Status of disease at transplant and graft composition in HLA haplotype-mismatched transplants with and without KIR ligand incompatibility in the GVH direction. *t(9;22) translocation, or bulky disease, or first-line induction therapy failure; †myelodysplasia, or unfavorable cytogenetics, or first-line induction therapy failure; ‡N.S. by two-tailed Student's t-test.

| KIR ligand incompatibility in GvH direction | NO (n = 58) | YES (n = 34) |
|---|---|---|
| Status of disease at transplant: | | |
| ALL | 21 | 14 |
| bad-risk* $1^{st}$ or $2^{nd}$ complete remission | 3/21 | 2/14† |
| $3^{rd}$ complete remission or relapse | 18/21 | 12/14† |
| AML | 37 | 20 |
| bad-risk† $1^{st}$ or $2^{nd}$ complete remission | 7/37 | 3/20† |
| 3rd complete remission or relapse | 30/37 | 17/20† |
| Graft composition (mean ± s.d.): | | |
| CD34+ × $10^6$/Kg | 15 ± 5.1 | 14.5 ± 5.1‡ |
| CD3+ × $10^4$/Kg | 3.5 ± 4.3 | 3.9 ± 4.6‡ |

Methods

Human transplantation. Patients were conditioned with TBI, thiotepa, anti-thymocyte globulin and fludarabine (1, 2), except for 26 who received cyclophosphamide instead of fludarabine (3).

T cell depletion of donor granulocyte-colony stimulating factor-mobilized blood cells was by soybean agglutination and E-rosetting in the first 26 transplants (3) (graft, 14±6×$10^6$ CD34+ and 1.5±5×$10^5$ CD3+ cells/Kg), E-rosetting and CD34+ cell selection with Cell Pro columns (Bothell, Wash.) in 44 transplants (1) (graft, 15±6×$10^6$ CD34+ and 3.5±4.2× $10^4$ CD3+ cells/Kg), Clinimacs CD34( cell selection (Miltenyi, Bergisch Gladbach, Germany) in the last 22 transplants (1, 2) (graft, 18±5×$10^6$ CD34+ and 3±3×$10^4$ CD3+ cells/Kg). No post-grafting GVHD prophylaxis was given.

Blood and marrow chimerism was assessed bi-monthly by PCR amplification of variable-number tandem repeat regions with different DNA polymorphism patterns (DNA microsatellites) (4). All assessments showed 100% donor chimerism.

Preparation of human NK clones. Blood mononuclear cells depleted of T cells by negative anti-CD3 immuno-magnetic selection (Miltenyi) were plated under limiting-dilution conditions, activated with phytohemagglutinin (PHA) (Biochrom KG, Berlin, Germany), and cultured with interleukin (IL)-2 (Chiron B.V., Amsterdam, Netherlands) and irradiated feeder cells (5). Cloning efficiencies were equivalent in all donors and ranged between 1 in 5 and 1 in 10 plated NK cells. Cloned NK cells were screened for alloreactivity by standard 51Cr release cytotoxicity against recipient PHA lymphoblasts, or Epstein-Barr virus-transformed B lymphoblastoid cell lines at an effector to target ratio of 10:1. Clones exhibiting ≧30% lysis were scored as alloreactive. As a rule, clones either exhibited<5% or>40% lysis. Bulk NK cells were not used because alloreactivity can be detected only when>1 in 5 cells are alloreactive.

Preparation of human leukemia-engrafted mice. 3.5 Gy-irradiated NOD-SCID mice, (Charles River Italia, Calco, Italy) were given 2×$10^7$ human leukemia cells. Six weeks later, spleen and bone marrow leukemic infiltration was detected by flow-cytometry (FCM) using FITC-labeled antihuman CD45 mAb, and by PCR analysis of DNA microsatellites (for AML) (4) or of the BCR/ABL gene (for chronic myeloid leukemia, CML) (6).

Murine transplantation. Recipient mice were C57BL/6 (B6, H-$2^b$), or DBA/2 or BALB/c (H-$2^d$). Donor mice were (C57BL/6×DBA2)$F_1$ or (C57BL/6×BALB/c)$F_1$ (H-$2^{d/b}$). Recipients were conditioned with TBI, or with chemotherapy, and NK cells were infused intravenously four days later. 1-2×$10^7$ donor marrow cells were T-cell depleted by negative immunomagnetic selection using fluorescein isothiocyanate (FITC)-conjugated anti-CD3e monoclonal antibody (mAb) (PharMingen, San Diego, Calif.) and anti-FITC antibody-coated beads (Polysciences, Warrington, Pa.), and infused intravenously 1 day after conditioning. Allogeneic reconstitution of T cells and granulocytes was evaluated by two-color immunofluorescence and FCM with anti-CD4 (anti-CD8, and anti-Gr-1, respectively (anti-H-$2D^d$ or anti-H-$2K^b$ mAb (PharMingen). Donor chimerism was assessed one, four and six months after transplant. GVHD was monitored by survival and by development of weight loss and alopecia.

Preparation of murine NK cells. After red blood cell lysis, monocyte adhesion to plastic, and Fc receptor blockade with anti-FcRIII mAb, NK cell subsets were obtained from splenocytes by negative immunomagnetic depletion of T and B cells, and granulocytes with FITC-conjugated anti-CD3e, anti-IgM, and anti-Gr-1 mAb (PharMingen), and anti-FITC antibody-coated beads (Polysciences). Cells were cultured for 4 days with human IL-2 (Chiron). Ly49A/G2+/Ly49C/I$^-$ and Ly49A/G2$^-$/Ly49C/I$^+$ NK cells were purified (>98%) by cell sorting (FACScalibur, Becton-Dickinson, San Jose, Calif.) using FITC-coniugated anti-Ly49A ( anti-Ly49G2, and PE-coniugated anti-Ly49C/I mAb (PharMingen), and assayed for alloreactivity by using H-$2^b$ or H-$2^d$ Concanavalin A (Sigma, Saint Louis, Mo.) blasts as targets. Alloreactive NK cells were used for in vivo experiments, with non-alloreactive cells as controls. Some experiments were performed with unseparated NK cells, and yielded identical results provided the absolute number of alloreactive cells stayed the same (7).

Preparation of chimeras and assessment of APC chimerism. B6 (H-$2^b$) mice received 9 Gy TBI and T-depleted BMT from B6×BALB/c (H-$2^{d/b}$) or B6 (H-$2^b$) mice. Four months later, chimeras were reirradiated with two 4 Gy fractions, then injected with 1-2×$10^7$ T-depleted allogeneic H-$2^d$ bone marrow cells with or without increasing doses of H-$2^d$ T cells. APC (dendritic cell) chimerism was evaluated by two color FCM with anti-CD11c (anti-H-$2D^d$ or anti-H-$2K^b$ mAb. Gut dendritic cells were isolated by collagenase type IV digestion of Payer's patches and intestinal tissue, and 40-70% Percoll gradient centrifugation.

Additional Experiments

Our mouse models demonstrate alloreactive NK cells ablate leukemia, condition to engraftment, and protect from GVHD. For these reasons, we planed on conducting a phase I clinical trial of the adoptive transfer of alloreactive NK cells in a reduced intensity conditioning regimen for high risk AML patients with an indication to transplant, who do not have a matched donor and who are unable to withstand the toxicity of current high intensity conditioning regimens. The reduced-intensity version, i.e., with Melphalan and Thiotepa at about half the original dose is supplemented with donor alloreactive NK clones. The procedure for preparing the NK clones requires: a) selection of NK alloreactive donors, b) generation of large numbers of NK clones, c) screening of clones for lysis of recipient cells, and d) expansion of each alloreactive clone to approximatively 20-30 million cells.

Results of the few transplants that have attempted so far with this pilot study are promising as 4 out of 4 engraftments have been achieved and, as expected from the mouse experiments, there was no VGHD, or other toxicity.

Adoptive Transfer of Alloreactive NK cells in a reduced-intensity conditioning regimen of one HLA haplotype mismatched hematopoietic transplantation Donor Selection The NK cell donor will be selected on the basis of the donor-versus-recipient NK alloreactivity (see APPENDIX A). The NK cell donor may not need to be the stem cell donor. This will allow banking of alloreactive clones with known allospecificity ahead of time.

Donor selection will be based on typing of HLA-A,B,C, DR loci to be carried out on the recipient, siblings, parents and if required, other family members such as aunts, uncles and cousins. The donor must be at least genotypically HLA-A,B, C, DR haploidentical to the patient, but can differ for 2-3 HLA alleles on the unshared haplotype.

Mobilization Therapy

At least one week before the patient starts conditioning for the transplant, the donor will receive G-CSG (either filgrastim or lenograstim) at either 12 μg/kg/day in a continuous subcutaneous infusion or 8 μg/kg/day in two push doses (every 12 hours) for 7 days.

Stem Cell Collection and Processing

On the fourth day of this course of G-CSF, if the circulating CD34 counts is>40/μl the donor will start leukapheresis which will continue for three consecutive days. Normal access is through a peripheral vein; central venous access may be required in exceptional cases.

Each leukapheresis product will be processed by the Clinimacs and cryopreserved until used.

Essential graft parameters are a minimum of 8×$10^6$ CD34+ cells/kg recipient b.w. and a maximum of 1×$10^4$ CD3+ cells/kg recipient b.w. If the targets are not reached a different suitable haploidentical donor will be mobilized.

Preparation of Donor Versus Recipient Alloreactive NK Clones

Four to six weeks before transplant a 10 ml blood sample will be taken from each donor in order to make alloreactive NK clones to be used for conditioning. The procedure for preparing the NK clones requires a) selection of GvH KIR epitope-mismatched donors, b) the generation of large numbers (e.g., 500) of NK clones, c) the screening of such clones for lysis of recipient cells, d) expansion of each alloreactive clone (generally found in the frequency of 1 in 10) to approximately 20-30 million.

- Blood mononuclear cells are depleted of T cells by negative anti-CD3 immuno-magnetic selection (Miltenyi)
- Cells are plated under limiting-dilution conditions in 96-well plates (5-10 NK cells per well).
- Typically, 50 plates are necessary for each preparation. (We usually prepare a back-up dose with another 50 plates).
- At least 300-500 NK clones must be obtained in order to identify 30-50 alloreactive ones (frequency=1:5-1:20).
- Day 0, plated cells are activated with PHA in the presence of irradiated feeder cells (buffycoats from Blood Bank).
- Day+1, IL-2 is added (1000 IU/ml).
- Day 6, fresh IL-2 media+feeder cells added.
- At 2 weeks, wells containing growing cultures are discriminated (from wells containing only feeder cells) by screening plates with an inverted microscope. Growing culture are split as necessary and supplemented with IL-2, feeder cells, and the RPMI-8866 EBV cell line.

At 3 weeks, 300-500 NK clones are screened for alloreactivity by standard 51Cr release cytotoxicity against recipient PHA lymphoblasts, or EBV cell lines at an effector to target ratio of 10:1. Clones exhibiting 50% lysis are scored as alloreactive.

Weeks 3-6. The selected 30-50 alloreactive clones are expanded to approximately 20 million cells each and frozen (total dose 600-1,000×10$^6$).

Patient Bone Marrow Harvest

Patients in remission before transplant will undergo bone marrow harvest.

Conditioning Regimen

Cytoreduction will be performed with ATG 5 mg/day for 4 days (e.g. days -9, -8, -7, -6), Fludarabine 40mg/m$^{2/}$day for 5 days (e.g. days -9, -8, -7, -6, -5), Melphalan 70 mg/m$^2$ in a single dose (e.g. day -8), Thiotepa 5mg/Kg in a single dose (e.g. day -9), and the infusion of donor alloreactive NK clones at the dose of 10-30×10$^6$ cell/Kg body weight (e.g. day-2). Before infusion of the alloreactive NK clones patients will undergo plasmapheresis to remove circulating ATG because of its known reactivity against NK cells.

Transplant

On Day 0, the graft is rapidly thawed and infused through a central line following standard procedure and safety measures.

Post-Transplant Treatment

No immunosuppressive treatment will be given as prophylaxis for GvHD. No G-CSF will be administered.

APPENDIX A

Work-up for NK Alloreactive Donor Selection

Current criteria for donor selection for haploidentical transplants. For AML, donor selection may now involve, not only standard donor inclusion criteria, but also a deliberate search for the "perfect mismatch" (Kärre 2002) at certain HLA loci —that is, for the mismatch that drives donor-vs-recipient NK cell alloreactivity. Haploidentical donors can be selected for KIR ligand mismatches (on the unshared haplotype) in the graft-versus-host direction. Selection for KIR mismatching is based on HLA typing as performed by serological and high-resolution molecular techniques. The search for NK alloreactive donors may require extension from the immediate family (parents and siblings) to other family members such as aunts, uncles and cousins. Such an extended search raises the chance of finding an NK alloreactive donor from the random 30% to>60% (which is close to the maximum, bearing in mind that HLA type of about 30% of the population makes them resistant to alloreactive NK killing, see above).

For NK alloreactive donor selection, first type the recipient. Recipients who express class I alleles belonging to the 3 major class I groups (HLA-C group 1, HLA-C group 2, and HLA-Bw4 alleles) will block all NK cells from every donor. Recipients who express alleles belonging to only 1 or 2 of these three class I groups, have the chance of finding NK alloreactive donors. Donor typing will then proceed to find the relative who expresses the allele in the class I group that is not expressed by the patient. Table 5 shows HLA-C group 1, and HLA-C group 2 alleles, along with the amino acid sequences which is the basis of the group classification. As new alleles are discovered, they are grouped according to their amino acid sequence. Table 2 also includes HLA-B alleles sharing the Bw4 supertypic specificity.

Several donor-recipient combinations are possible which based on current knowledge are reported in Table 3. When, for example, the recipient's HLA type contains HLA-C group 1, HLA-C group 2, HLA-Bw4 alleles no NK alloreactive donor can be found. If the recipient expresses Group 1 and Group 2 HLA-C alleles (but not Bw4 alleles), the donor must have a Bw4 allele (in addition to whatever other allele groups) in order to provide NK alloreactivity. Should the recipient express Group 1 HLA-C alleles and HLA-Bw4 alleles, the donor must have a Group 2 HLA-C allele in order to be NK alloreactive. When the recipient expresses Group 2 HLA-C and HLA-Bw4 alleles, the donor needs to have a Group 1 HLA-C allele. In the case that the recipient expresses Group 1 HLA-C alleles only, the donor must have a Group 2 HLA-C allele, and/or an HLA-Bw4 allele to ensure NK alloreactions. Finally, if the recipient has a Group 2 HLA-C allele only, the donor must have a Group 1 HLA-C and/or an HLA-Bw4 allele. One very rare additional mismatch is the HLA-A3/11 negative recipient and HLA-A3/A11 positive donor. In the Ruggeri et al. study (2002) the HLA-A3/A11 mismatch was never found alone but only in conjunction with HLA-C group mismatches. Therefore, no prediction as to the efficacy of this mismatch combination can be made.

TABLE 2

List of Group 1 and group 2 HLA-C and HLA-Bw4 alleles

| Group 1 HLA-C alleles (Ser 77, Asn 80) | Group 2 HLA-C alleles (Asn 77, Lys 80) | HLA-Bw4 alleles |
|---|---|---|
| Cw1 (all)# | Cw2 (all) | B5 (all) |
| Cw3 (all except C*0307, C*0310 and C*0315) | C*0307 | B13 (all) |
| Cw7 (all except C*0707 and C*0709) | C*0315 | B17 (all) |
| Cw8 (all) | Cw4 (all) | B27 (all) |
| Cw12 (all except C*1205, C*12041, C*12042) | Cw5 (all) | B37 (all) |
| Cw13 (all) | Cw6 (all) | B38 (all) |
| Cw14 (all, except C*1404) C*1507 | C*0707 | B44 (all) |
| Cw16 (all except C*1602) | C*0709 | B47 (all) |
|  | C*1205 | B49 (all) |
|  | C*12041 | B51 (all) |
|  | C*12042 | B52 (all) |
|  | Cw15 (all except C*1507) | B53 (all) |
|  | C*1602 | B57 (all) |
|  | Cw17 (all) | B58 (all) |
|  | Cw18 (all) | B59 (all) |
|  |  | B63 (all) |
|  |  | B77 (all) |
|  |  | B*1513 |
|  |  | B*1516 |
|  |  | B*1517 |
|  |  | B*1523 |
|  |  | B*1524 |

"all"=all molecular types within a serologically-defined group of alleles.

N.B. C*0310 (Ser77, Lys80) behaves as if it belonged to Group 1 and to Group 2 HLA-C (Biassoni et al., 1995). If a patient expresses this allele he or she should be considered to express both allele groups. In other words, C*0310 blocks NK cells expressing any HLA-C-specific receptor, it does not block clones expressing the Bw4 receptor.

C*1404 (Asn77, Asn80) is the opposite. It does not belong to Group 1 or to Group 2 HLA-C (Biassoni et al., 1995). In other words, it does not block NK cells expressing HLA-C specific receptors. So, expression of C*1404 may be ignored in a patient, because it is as if the patient did not express HLA-C alleles at all. Of course one has to consider the other allele.

C*1207 Gly77, Asn80, cannot be assigned to either group based on its aminoacid sequence, and still needs to be tested functionally.

TABLE 3

Donor/recipient combinations predicting NK cell alloreactivity in the GvH direction. Whatever other alleles are present in the donor's HLA type, the ones listed here predict NK cell alloreactions against the specific HLA type of the recipient.

| Recipient HLA type | HLA type of NK alloreactive donor* |
|---|---|
| Group 1 HLA-C, Group 2 HLA-C, HLA-Bw4 | No NK alloreactive donor |
| Group 1 HLA-C, Group 2 HLA-C | HLA-Bw4 |
| Group 1 HLA-C, HLA-Bw4 | Group 2 HLA-C |
| Group 2 HLA-C, HLA-Bw4 | Group 1 HLA-C |
| Group 1 HLA-C | Group 2 HLA-C and/or HLA-Bw4 |
| Group 2 HLA-C | Group 1 HLA-C and/or HLA-Bw4 |

*In each recipient/donor combination the donor has an NK repertoire which contains NK cells that are specifically blocked by the allele group(s) indicated in the donor column. These NK cells will be alloreactive because the corresponding recipient does not express this allele group.

REFERENCES

Asai O, Longo D L, Tian Z G, Homung R L, Taub D D, Ruscetti F W, Murphy W J (1998)" Suppression of graft-versus-host disease and amplification of graft-versus-tumor effects by activated natural killer cells after allogeneic bone marrow transplantation" J. Clin. Invest., 101, 1835-42

Aversa F, Tabilio A, Terenzi A, Velardi A, Falzetti F, Giannoni C, Iacucci R, Zei T, Martelli M P, Gambelunghe C, et al., (1994) "Successful engraftment of T-cell-depleted haploidentical "three-loci" incompatible transplants in leukemia patients by addition of recombinant human granulocyte colony-stimulating factor-mobilized peripheral blood progenitor cells to bone marrow inoculum" Blood 84:3948-55

Aversa F, Tabilio A, Velardi A, Cunningham I, Terenzi A, Falzetti F, Ruggeri L, Barbabietola G, Aristei C, Latini P, Reisner Y, Martelli M F, (1998) "Treatment of high-risk acute leukemia with T-cell-depleted stem cells from related donors with one fully mismatched HLA haplotype" N Engl J Med 339:1186-93

Bachar-Lustig E, Rachamim N, Li H W, Lan F, Reisner Y, (1995)" Megadose of T cell-depleted bone marrow overcomes MHC barriers in sublethally irradiated mice" Nat Med 1:1268-73

Baum, C. M., I. L. Weissman et al., (1992) "Isolation of a candidate human hematopoietic stem-cell population" Proc. Natl. Acad. Sci. U.S.A. 89:2804-8

Bellone G, Valiante N M, Viale O, Ciccone E, Moretta L, Trinchieri G (1993) <<Regulation of hematopoiesis in vitro by alloreactive natural killer cell clones": J Exp Med 177:1117-25

Biassoni R, Falco M, Cambiaggi A, Costa P, Verdiani S, Pende D, Conte R, Di Donato C, Parham P, Moretta L (1995) "Amino acid substitutions can influence the natural killer (NK)-mediated recognition of HLA-C molecules. Role of serine-77 and lysine-80 in the target cell protection from lysis mediated by "group 2" or "group 1" NK clones" J Exp Med; 182:605-9

Blazer et al., (1985) "Comparison of three techniques for the ex vivo elimination of T cells from human bone marrow." Experimental Hematology 13:123-128

Caspar, C. B., Seger, R. A., Burger, J. and Gmur, J. (1993). Effective stimulation of donors for granulocyte transfusions with recombinant methionyl granulocyte colony-stimulating factor. Blood 81:2866-71.

Ciccone E, Pende D, Viale O, Di Donato C, Tripodi G, Orengo A M, Guardiola J, Moretta A, Moretta L (1992a) "Evidence of a natural killer (NK) cell repertoire for (allo) antigen recognition: definition of five distinct NK-determined allospecificities in humans": J Exp Med 175:709-18

Ciccone E, Pende D, Viale O, Than A, Di Donato C, Orengo A M, Biassoni R, Verdiani S, Amoroso A, Moretta A, et al. (1992b) "Involvement of HLA class I alleles in natural killer (NK) cell-specific functions: expression of HLA-Cw3 confers selective protection from lysis by alloreactive NK clones displaying a defined specificity (specificity 2)." J Exp Med 176:963-71

Colonna M, Brooks E G, Falco M, Ferrara G B, Strominger J L (1993a) "Generation of allospecific natural killer cells by stimulation across a polymorphism of HLA-C" Science 260:1121-4

Colonna M, Borsellino G, Falco M, Ferrara G B, Strominger J L (1993b) "HLA-C is the inhibitory ligand that determines dominant resistance to lysis by NK1- and NK2-specific natural killer cells" Proc Natl Acad Sci U S A 90:12000-4

Geiselhart A, Neu S, Buchholz F, Lang P, Niethammer D, Handgretinger R (1996-97) "Positive selection of CD56+ lymphocytes by magnetic cell sorting" Nat Immun 15:227-33

Giralt S, Slavin S (2000) Eds., Non-Myeloablative Stem Cell Transplantation (NST) (Darwin Scientific Publishing, Abington, UK)

Handgretinger R, Welte B, Dopfer R. Niethammer D (1994) "Rapid method for purification of CD56+ natural killer cells with preferential enrichment of the CD56bright+ subset" J Clin Lab Anal 8:443-6

Hosaka H, Surth CD, Sprent J (1992) J Exp Med 176:1291

Karre K, Ljunggren H G, Piontek G, Kiessling R, (1986) "Selective rejection of H-2-deficient lymphoma variants suggests alternative immune defence strategy" Nature 319: 675-8

Karre K (2002) "Immunology. A perfect mismatch" Science 295:2029-31

Lanier L L, Le A M, Phillips J H, Warner N L, Babcock G F (1983) "Subpopulations of human natural killer cells defined by expression of the Leu-7 (HNK-1) and Leu-11 (NK-15) antigens" J Immunol 131:1789-96

Lanier L L (1998) <<NK cell receptors" Annu Rev Immunol 16:359-93

Lansdorp, P. M., H. J. Sutherland et al., (1990) "Selective expression of CD45 isoforms on functional subpopulations of CD34+ hematopoietic cells from human bone marrow." J. Exp. Med. 172:363-6

Martelli M F, Aversa F, Bachar-Lustig E, Velardi A, Reich-Zelicher S, Tabillo A, Gur H, Reisner Y, (2002) "Transplants across human leukocyte antigen barriers" Semin Hematol 39:48-56

Moretta A, Moretta L (1997) <<HLA class I specific inhibitory receptors" Curr Opin Immunol 9:694-701

Ohlen C, Kling G, Hoglund P, Hansson M, Scangos G, Bieberich C, Jay G, Karre K (1989) "Prevention of allogeneic bone marrow graft rejection by H-2 transgene in donor mice" Science 246:666-8

Reisner, Y., Kapoor, N., Kirkpatrick, D., Pollack, M. S., Dupont, B., Good, R. A. and O'Reilly, R. J. (b 19811 ). Transplantation for acute leukemia with HLA-A and B non-identical parental marrow cells fractionated with soybean agglutinin and sheep red blood cells. Lancet ii:327.

Reisner, Y., Freidrich, W. and Fabian, I. (1986). A shorter procedure for preparation of E-rosette-depleted bone marrow for transplantation. Transplantation 42:312.

Reisner Y, Martelli M F, (1999) "Stem cell escalation enables HLA-disparate haematopoietic transplants in leukaemia patients" Immunol Today 20:343-7

Ruggeri L, Capanni M, Casucci M, Volpi I, Tosti A, Perruccio K, Urbani E, Negrin R S, Martelli M F, Velardi A (1999) "Role of natural killer cell alloreactivity in HLA-mismatched hematopoietic stem cell transplantation" Blood 94:333-9

Sato, N., K. Sawada et al., (1991) "Purification of human marrow progenitor cells and demonstration of the direct action of macrophage colony-stimulating factor on colony-forming unit-macrophage" Blood 78:967-74

W. D. Shlomchik, M. S. Couzens, C. Bi Tang, J. McNiff, M. E. Robert, J. Liu, M. J. Shlomchik, and S. G. Emerson (1999) <<Prevention of Graft Versus Host Disease by Inactivation of Host Antigen-Presenting Cells" Science 285, 412-15

Smith, C., C. Gasparetto et al., (1991) "Purification and partial characterization of a human hematopoietic precursor population" Blood 77:2122-8;

Stockerl-Golstein, K E, Blume K G, in Hematopoietic Cell Transplantation, E D Thomas, K G Blume, S J Forman, Eds. (Blackwell Science, Malden, Mass., 1999), pp. 823-834.

Timonen T, Reynolds C W, Ortaldo J R, Herberman R B, (1982)" Isolation of human and rat natural killer cells" J. Immunol. Methods, 51, 269-77

Udomsakdi, C., C. J. Eaves et al., (1991) "Separation of functionally distinct subpopulations of primitive human hematopoietic cells using rhodamine-123" Exp. Hematol. 19:338-42;

Udomsakdi, C., P. M. Lansdorp et al., (1992) "Characterization of primitive hematopoietic cells in normal human peripheral blood" Blood 80:2513-21

Valiante N M, Lienert K, Shilling H G, Smits B J, Parham P (1997a) <<Killer cell receptors: keeping pace with MHC class I evolution" Immunol Rev 155:155-64

Valiante N M, Parham P (1997b) <<Natural killer cells, HLA class I molecules, and marrow transplantation" Biol Blood Marrow Transplant 3:229-35

Zarling J M, Clouse K A, Biddison W E, Kung P C, (1981) "Phenotypes of human natural killer cell populations detected with monoclonal antibodies" J. Immunol. 127, 2575-80

All references cited herein are incorporated herein in their entirety by reference.

What is claimed:

1. A method of transplanting an allogeneic hematopoietic graft into a human subject in need thereof, comprising:
 a) providing active alloreactive donor-vs-recipient human natural killer cells which do not possess a killer cell inhibitory receptor (KIR) that is able to bind MHC/HLA antigen of said human subject;
 b) administering to said subject at least about $0.05 \times 10^6$ of said active alloreactive donor-vs.-recipient human natural killer cells per kilogram (kg) of body weight of said human subject; and
 c) transplanting said allogeneic hematopoietic graft into said subject.

2. A method of reducing Graft-versus-host disease (GVHD) in a human subject undergoing allogeneic hematopoietic graft, comprising:
 a) providing active alloreactive donor-vs-recipient human natural killer cells which do not possess a killer cell inhibitory receptor (KIR) that is able to bind MHC/HLA antigen of said human subject;
 b) administering to said subject at least about $0.05 \times 10^6$ of said active alloreactive donor-vs.-recipient human natural killer cells per kg of body weight of said human subject; and
 c) transplanting said allogeneic hematopoietic graft into said subject, wherein the administration of said alloreactive natural killer cells reducing GVHD in said subject.

3. A method of treating a human subject having a hematologic disorder, comprising transplanting an allogeneic hematopoietic graft into said subject so as to treat said disorder, providing active alloreactive donor-vs-recipient human natural killer cells which do not possess a killer cell inhibitory receptor (KIR) that is able to bind MHC/HLA antigen of said human subject, and administering to said human subject at least about $0.05 \times 10^6$ of said active alloreactive donor-vs.-recipient human natural killer cells per kg of body weight of said human subject.

4. A method of treating or preventing an infection in a subject undergoing allogeneic hematopoietic graft comprising:
 a) providing active alloreactive donor-vs-recipient human natural killer cells which do not possess a killer cell inhibitory receptor (KIR) that is able to bind MHC/HLA antigen of said human subject;
 b) administering to said subject at least about $0.05 \times 10^6$ of said active alloreactive donor-vs-recipient human natural killer cells per kg of body weight of said human subject; and,
 c) transplanting into said subject said allogeneic hematopoietic graft, said hematopoietic graft comprising T cells which are effective in treating or preventing said infection.

5. A method of increasing engraftment or for reducing hematopoietic graft rejection in a human subject undergoing allogeneic graft, the method comprising:
 a) providing active alloreactive donor-vs-recipient human natural killer cells which do not possess a killer cell inhibitory receptor (KIR) that is able to bind MHC/HLA antigen of said human subject;
 b) administering to said subject at least about $0.05 \times 10^6$ of said active alloreactive donor-vs-recipient human natural killer cells per kg of body weight of said human subject; and,
 c) transplanting into said human subject said hematopoietic allogeneic graft,
 the active alloreactive human natural killer cells causing increased engraftment or decreased graft rejection.

6. A method of reducing the intensity of conditioning regimen for a human subject in need of an allogeneic hematopoietic graft, comprising:
 a) providing active alloreactive donor-vs-recipient human natural killer cells which do not possess a killer cell inhibitory receptor (KIR) that is able to bind MHC/HLA antigen of said human subject;

b) administering to said human subject at least about $0.05 \times 10^6$ of said active alloreactive donor-vs-recipient human natural killer cells per kg of body weight of said human subject, in combination with the administration of the reduced-intensity conditioning regimen; and, c) transplanting said allogeneic hematopoietic graft into human said subject.

7. The method of claim 1, wherein said natural killer cells and said allogeneic hematopoietic graft are administered into said human subject simultaneously.

8. The method of claim 1, wherein said natural killer cells are administered prior to said allogeneic hematopoietic graft.

9. The method of any one of claims 1, 2, 3, 4, 5 or 6, wherein said hematopoietic graft is a bone marrow transplant.

10. The method of claim 1, wherein said human subject is treated under myelo-reductive regimen before said transplantation of said allogeneic hematopoietic graft.

11. The method of claim 1, wherein said active alloreactive natural killer cells are prepared by:
   providing natural killer cells from an alloreactive human donor;
   culturing said natural killer cells in the presence of interleukin-2; and,
   collecting the active alloreactive donor-vs-recipient natural killer cells.

12. The method of claim 11, wherein said active alloreactive natural killer cells are prepared by:
   providing natural killer cells from an alloreactive human donor;
   isolating said natural killer cells;
   culturing said natural killer cells in the presence of IL-2,
   testing the alloreactivity of said active natural killer cells against recipient cells; and
   optionally, pooling the active alloreactive donor-vs-recipient natural killer cells.

13. The method of claim 1, wherein said human subject is treated for a myeloid leukemia.

14. The method of claim 3, wherein the hematologic disorder is selected from the group consisting of lymphoblastic leukemia, acute or chronic myelogenous leukemia, Hodgkin's lymphoma, Non-Hodgkin's lymphoma, myelodysplastic syndrome, multiple myeloma, and chronic lymphocytic leukemia.

15. The method of claim 3, wherein the hematologic disorder is mediated by cells susceptible to alloreactive natural killer cell killing.

16. The method of claim 3, wherein the hematologic disorder is acute myelogenous leukemia.

* * * * *